(12) United States Patent
Scheller et al.

(10) Patent No.: US 11,160,935 B2
(45) Date of Patent: Nov. 2, 2021

(54) REUSABLE INSTRUMENT HANDLE WITH SINGLE-USE TIP

(71) Applicant: Katalyst Surgical, LLC, Chesterfield, MO (US)

(72) Inventors: Gregg D Scheller, Wildwood, MO (US); Eric J Bass, Webster Groves, MO (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 742 days.

(21) Appl. No.: 15/604,844

(22) Filed: May 25, 2017

(65) Prior Publication Data

US 2017/0361034 A1    Dec. 21, 2017

Related U.S. Application Data

(60) Provisional application No. 62/350,989, filed on Jun. 16, 2016.

(51) Int. Cl.
*A61M 5/50* (2006.01)
*A61B 17/34* (2006.01)
(Continued)

(52) U.S. Cl.
CPC .............. *A61M 5/50* (2013.01); *A61B 17/29* (2013.01); *A61B 17/2909* (2013.01);
(Continued)

(58) Field of Classification Search
CPC combination set(s) only.
See application file for complete search history.

(56) References Cited

U.S. PATENT DOCUMENTS

| 1,736,731 A | 11/1929 | Breeding |
| 2,549,731 A | 4/1951 | Wattley |

(Continued)

FOREIGN PATENT DOCUMENTS

| WO | WO1997015234A1 A1 | 5/1997 |
| WO | WO1998037819 A1 | 9/1998 |

(Continued)

OTHER PUBLICATIONS

Steve Charles, Techniques and tools for dissection of epiretinal membranes, Graefe' Arch Clin Exp Ophthalmol, 241:347-352, 2003.

(Continued)

*Primary Examiner* — Scott Luan

(57) ABSTRACT

A reusable instrument handle with single-use tip may include an instrument tip and an instrument handle. The instrument tip may include an outer base, a nosecone, a pressure mechanism, a hypodermic tube, a blank, a fixation mechanism, and a tip cover. The instrument handle may include an actuation structure, a fixation mechanism receptacle, and an instrument tip housing. The fixation mechanism and the fixation mechanism receptacle may be configured to temporarily fix the instrument tip in the instrument tip housing. A compression of the actuation structure may be configured to actuate the hypodermic tube relative to the blank. The instrument tip may be removed from the instrument tip housing after use by removing the fixation mechanism from the fixation mechanism receptacle.

19 Claims, 9 Drawing Sheets

(51) Int. Cl.
*A61F 9/007* (2006.01)
*A61B 17/29* (2006.01)
*A61B 17/00* (2006.01)
*A61B 17/30* (2006.01)
*A61B 90/00* (2016.01)
*A61B 90/90* (2016.01)

(52) U.S. Cl.
CPC .......... *A61B 17/3494* (2013.01); *A61F 9/007* (2013.01); *A61B 90/90* (2016.02); *A61B 2017/0046* (2013.01); *A61B 2017/00477* (2013.01); *A61B 2017/00876* (2013.01); *A61B 2017/2916* (2013.01); *A61B 2017/305* (2013.01); *A61B 2017/347* (2013.01); *A61B 2090/0807* (2016.02)

(56) References Cited

U.S. PATENT DOCUMENTS

| | | |
|---|---|---|
| 3,659,607 A | 5/1972 | Banko |
| 4,135,868 A | 1/1979 | Schainholz |
| 4,504,246 A | 3/1985 | Kelman |
| 4,541,992 A | 9/1985 | Jerge et al. |
| 4,553,957 A | 11/1985 | Williams et al. |
| 4,610,252 A | 9/1986 | Catalano |
| 4,706,666 A | 11/1987 | Sheets |
| 4,739,761 A | 4/1988 | Grandon |
| 4,798,292 A | 1/1989 | Hauze |
| 4,959,199 A | 9/1990 | Brewer |
| 5,190,050 A | 3/1993 | Nitzsche |
| 5,215,726 A | 6/1993 | Kudla et al. |
| 5,222,973 A | 6/1993 | Sharpe et al. |
| 5,227,313 A | 7/1993 | Gluck et al. |
| 5,286,255 A | 2/1994 | Webber |
| 5,318,589 A | 6/1994 | Lichtman |
| 5,346,677 A | 9/1994 | Risk |
| 5,355,871 A | 10/1994 | Hurley et al. |
| 5,370,658 A | 12/1994 | Scheller et al. |
| 5,384,103 A | 1/1995 | Miller |
| 5,415,645 A | 5/1995 | Friend et al. |
| 5,425,730 A | 6/1995 | Luloh |
| 5,433,929 A | 7/1995 | Riihimaki et al. |
| 5,451,230 A | 9/1995 | Steinert |
| 5,527,313 A | 6/1996 | Scott et al. |
| 5,601,581 A | 2/1997 | Fogarty et al. |
| 5,636,639 A | 6/1997 | Turturro et al. |
| 5,695,514 A | 12/1997 | Chin |
| D393,067 S | 3/1998 | Geary et al. |
| D393,715 S | 4/1998 | Strickland |
| 5,759,502 A | 6/1998 | Spencer et al. |
| 5,792,165 A | 8/1998 | Klieman et al. |
| 5,810,811 A | 9/1998 | Yates et al. |
| 5,843,387 A | 12/1998 | Dane et al. |
| 5,851,197 A | 12/1998 | Marano et al. |
| 5,893,873 A | 4/1999 | Rader et al. |
| 5,893,877 A | 4/1999 | Gampp, Jr. et al. |
| 5,913,422 A | 6/1999 | Cote et al. |
| 5,916,159 A | 6/1999 | Ryan, Jr. |
| 5,921,998 A | 7/1999 | Tano et al. |
| 6,099,550 A | 8/2000 | Yoon |
| 6,159,162 A | 12/2000 | Kostylev et al. |
| 6,183,467 B1 | 2/2001 | Shapeton et al. |
| 6,277,100 B1 | 8/2001 | Raulerson et al. |
| D453,222 S | 1/2002 | Garito et al. |
| 6,419,675 B1 | 7/2002 | Gallo, Sr. |
| D463,555 S | 9/2002 | Etter et al. |
| 6,488,695 B1 | 12/2002 | Hickingbotham |
| 6,551,129 B2 | 4/2003 | Kato |
| 6,572,565 B2 | 6/2003 | Daley et al. |
| 6,575,989 B1 | 6/2003 | Scheller et al. |
| 6,616,683 B1 | 9/2003 | Toth et al. |
| 6,730,076 B2 | 5/2004 | Hickingbotham |
| 6,749,601 B2 | 6/2004 | Chin |
| 6,800,076 B2 | 10/2004 | Humayun |
| 6,863,668 B2 | 3/2005 | Gillespie et al. |
| 6,908,476 B2 | 6/2005 | Jud et al. |
| 6,926,728 B2 | 8/2005 | Zucherman et al. |
| 6,945,984 B2 | 9/2005 | Arumi et al. |
| 7,338,494 B2 | 3/2008 | Ryan |
| D565,733 S | 4/2008 | Andre |
| 7,438,717 B2 | 10/2008 | Tylke |
| 7,632,242 B2 | 12/2009 | Griffin et al. |
| 7,731,728 B2 | 6/2010 | Glaser |
| 7,766,904 B2 | 8/2010 | McGowan, Sr. et al. |
| 7,783,346 B2 | 8/2010 | Smith et al. |
| D625,412 S | 10/2010 | Garito et al. |
| 7,935,080 B2 | 5/2011 | Howell et al. |
| 8,038,692 B2 | 10/2011 | Valencia et al. |
| 8,197,468 B2 | 6/2012 | Scheller et al. |
| 8,202,288 B2 | 6/2012 | Ryan |
| 8,821,444 B2 | 9/2014 | Scheller et al. |
| 9,138,346 B2 | 9/2015 | Scheller et al. |
| 9,149,389 B2 | 10/2015 | Scheller et al. |
| 9,204,995 B2 | 12/2015 | Scheller et al. |
| 9,226,762 B2 | 1/2016 | Scheller et al. |
| 9,427,251 B2 | 8/2016 | Rethy et al. |
| 2001/0056286 A1 | 12/2001 | Etter et al. |
| 2002/0115902 A1 | 8/2002 | Dejuan, Jr. et al. |
| 2003/0171762 A1 | 9/2003 | Forchette et al. |
| 2003/0229976 A1 | 12/2003 | Scheller et al. |
| 2005/0154403 A1 | 7/2005 | Sauer et al. |
| 2005/0245950 A1 | 11/2005 | Kozlowski |
| 2006/0036270 A1 | 2/2006 | Terao |
| 2006/0235382 A1 | 10/2006 | Cohen et al. |
| 2007/0104609 A1 | 5/2007 | Powell |
| 2007/0106246 A1 | 5/2007 | Modesitt |
| 2007/0185514 A1 | 8/2007 | Kirchhevel |
| 2007/0282348 A1 | 12/2007 | Lumpkin |
| 2008/0183199 A1 | 7/2008 | Attinger |
| 2008/0195135 A1 | 8/2008 | Attinger |
| 2008/0255526 A1 | 10/2008 | Bosse et al. |
| 2009/0030427 A1 | 1/2009 | Razvi et al. |
| 2009/0112258 A1 | 4/2009 | Kreidler |
| 2009/0131870 A1 | 5/2009 | Fiser |
| 2009/0228066 A1 | 10/2009 | Hirata et al. |
| 2009/0318856 A1 | 12/2009 | Glaser |
| 2010/0023050 A1 | 1/2010 | Reinauer et al. |
| 2010/0063359 A1 | 3/2010 | Okoniewski |
| 2010/0145381 A1 | 6/2010 | Moon |
| 2010/0228226 A1 | 9/2010 | Nielsen |
| 2011/0015669 A1 | 1/2011 | Corcosteugi |
| 2012/0116361 A1* | 5/2012 | Hanlon ................. A61F 9/007 606/1 |
| 2012/0150216 A1 | 6/2012 | Hickingbotham et al. |
| 2012/0179172 A1 | 7/2012 | Paul, Jr. et al. |
| 2012/0191120 A1 | 7/2012 | Linsi |
| 2013/0071507 A1 | 3/2013 | Scheller et al. |
| 2013/0085326 A1 | 4/2013 | Scheller et al. |
| 2013/0197488 A1 | 8/2013 | Scheller et al. |
| 2014/0012314 A1 | 1/2014 | Dai et al. |
| 2014/0066977 A1 | 3/2014 | Scheller et al. |
| 2014/0121697 A1 | 5/2014 | Scheller et al. |
| 2014/0128909 A1 | 5/2014 | Scheller et al. |
| 2014/0135820 A1 | 5/2014 | Schaller et al. |
| 2014/0142603 A1 | 5/2014 | Scheller et al. |
| 2014/0163363 A1 | 6/2014 | Scheller et al. |
| 2014/0172010 A1 | 6/2014 | Vezzu |
| 2014/0277110 A1 | 9/2014 | Scheller et al. |
| 2015/0088193 A1 | 3/2015 | Scheller et al. |
| 2015/0173944 A1 | 6/2015 | Linsi et al. |

FOREIGN PATENT DOCUMENTS

WO    WO2002041796 A2    5/2002
WO    WO2017066026 A1    4/2017

OTHER PUBLICATIONS http://www.bpf.co.uk/plastipedia/polymers/polyamides.aspx [Mar. 20, 2017 4:57:01 PM].

* cited by examiner

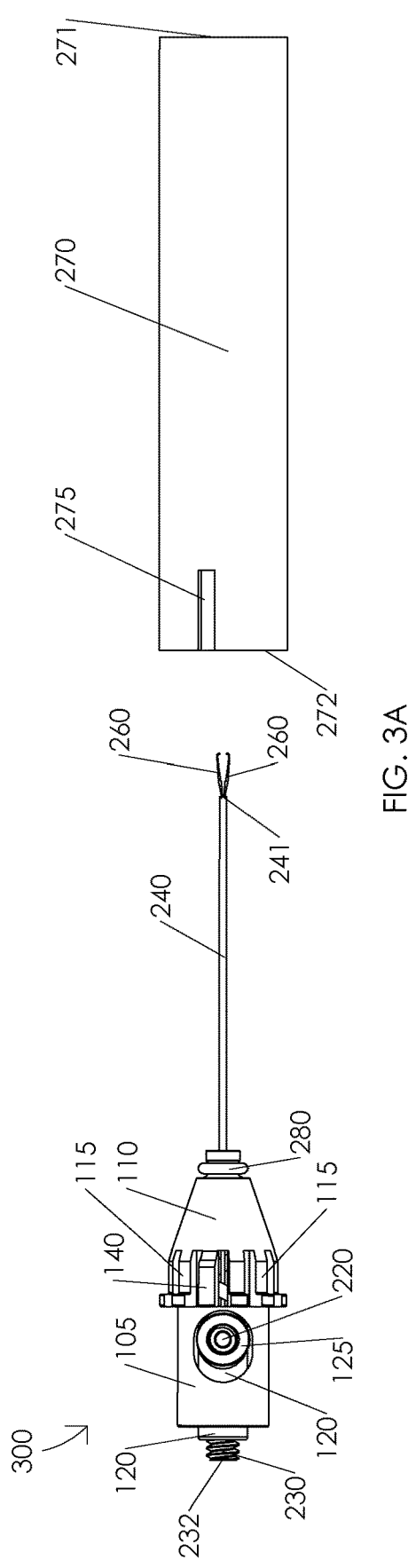
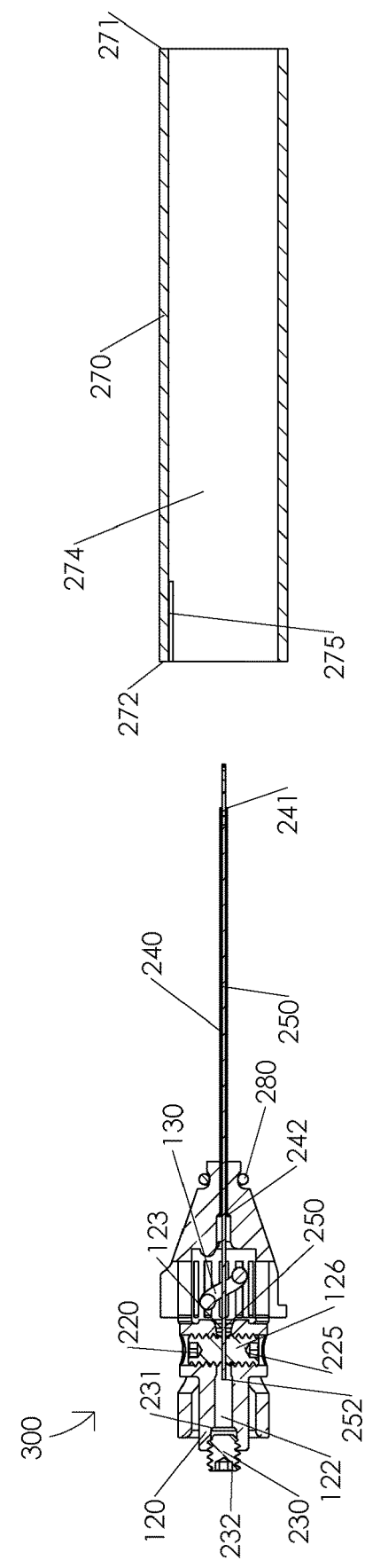
FIG. 3A
FIG. 3B

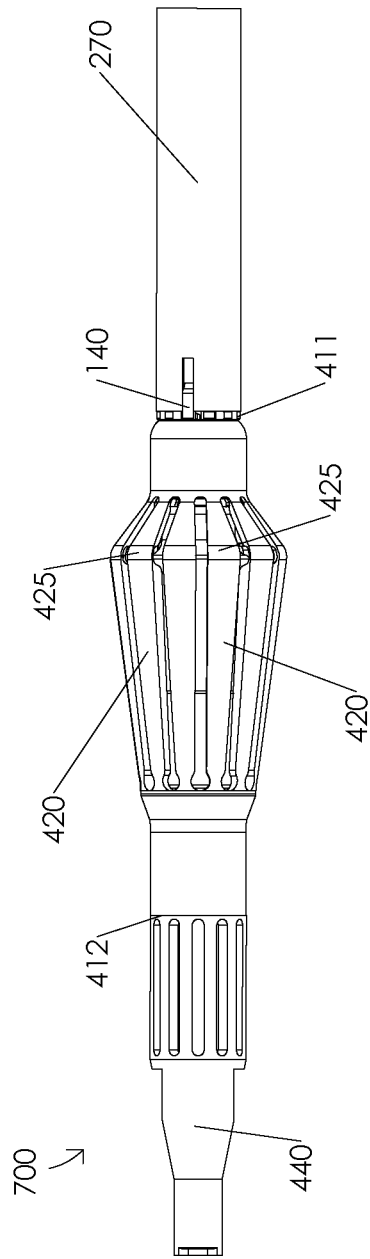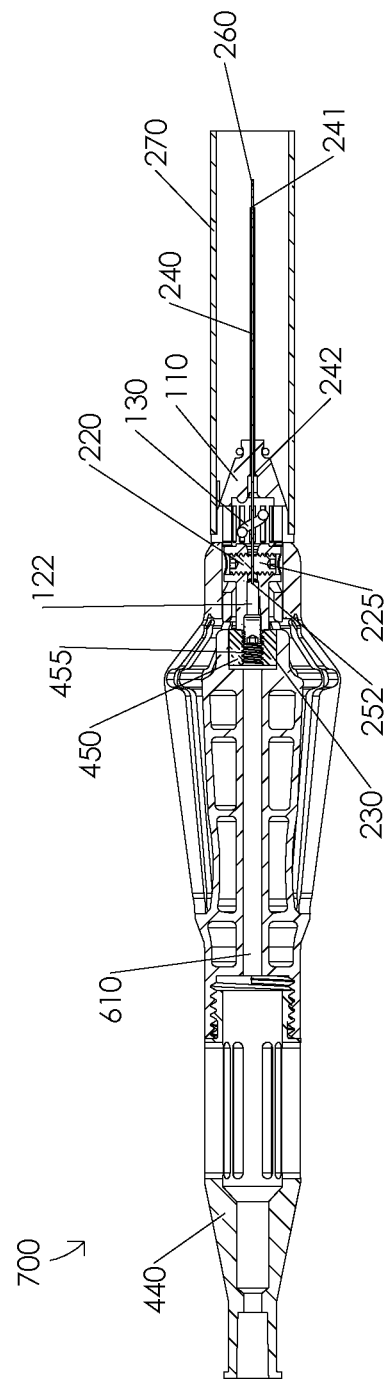
FIG. 7A
FIG. 7B

US 11,160,935 B2

REUSABLE INSTRUMENT HANDLE WITH SINGLE-USE TIP

CROSS-REFERENCE TO RELATED APPLICATIONS

This Application claims the benefit of U.S. Provisional Application No. 62/350,989, filed Jun. 16, 2016.

FIELD OF THE INVENTION

The present disclosure relates to a medical device, and, more particularly, to a surgical instrument.

BACKGROUND OF THE INVENTION

A variety of surgical procedures are performed through a very small surgical incision in a particular tissue. Reducing the size of a surgical incision during a surgical procedure generally reduces the amount of trauma to the surgical site and generally facilitates faster wound healing. In order to perform surgical procedures through a very small surgical incision, a surgeon may require specialized surgical instruments configured to fit through the very small surgical incision and provide the surgeon with a surgical utility. Sometimes a surgeon may require a surgical utility that may not be easily controlled close to a particular surgical site, e.g., closing forceps jaws inside of an eye. It is generally desirable for a surgeon to be able to control such a surgical utility with a minimal amount of effort. For example, if a surgical utility is controlled by a lever or a switch on an instrument handle, a surgeon may need to adjust an orientation of a surgical instrument in order to actuate the lever or the switch. Additionally, if a surgical utility control mechanism requires a surgeon to apply a significant amount of force to a portion of a surgical instrument, then it may be difficult for the surgeon to manipulate the surgical utility control mechanism without unintentionally moving a portion of the surgical instrument.

Ophthalmic surgical instruments are generally categorized as either reusable or single-use. A single-use instrument is typically sterilized prior to sale and is shipped to a surgery center sterile and ready for use in a surgical procedure. A reusable instrument is typically shipped to a surgery center non-sterile and is sterilized by the surgery center between uses in surgery. Reusable instruments are generally lower in overall cost for a surgery center compared to single-use instruments. Single-use instruments offer a surgery center greater convenience compared to reusable instruments. Accordingly, there is a need for an instrument that offers a surgery center the convenience of a single-use instrument at the overall lower cost of a reusable instrument.

BRIEF SUMMARY OF THE INVENTION

The present disclosure provides a reusable instrument handle with single-use tip. Illustratively, an instrument tip may comprise an outer base, a nosecone, a pressure mechanism, a hypodermic tube, a blank, a fixation mechanism, and a tip cover. In one or more embodiments, an instrument handle may comprise an actuation structure, a fixation mechanism receptacle, and an instrument tip housing. Illustratively, the fixation mechanism and the fixation mechanism receptacle may be configured to temporarily fix the instrument tip in the instrument tip housing. In one or more embodiments, a compression of the actuation structure may be configured to actuate the hypodermic tube relative to the blank. Illustratively, the instrument tip may be removed from the instrument tip housing after use by removing the fixation mechanism from the fixation mechanism receptacle.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 3A, 3B, 3C, and 3D are schematic diagrams illustrating an assembled instrument tip;

FIGS. 7A and 7B are schematic diagrams illustrating an assembled instrument.

DETAILED DESCRIPTION OF AN ILLUSTRATIVE EMBODIMENT

Figure 1A:
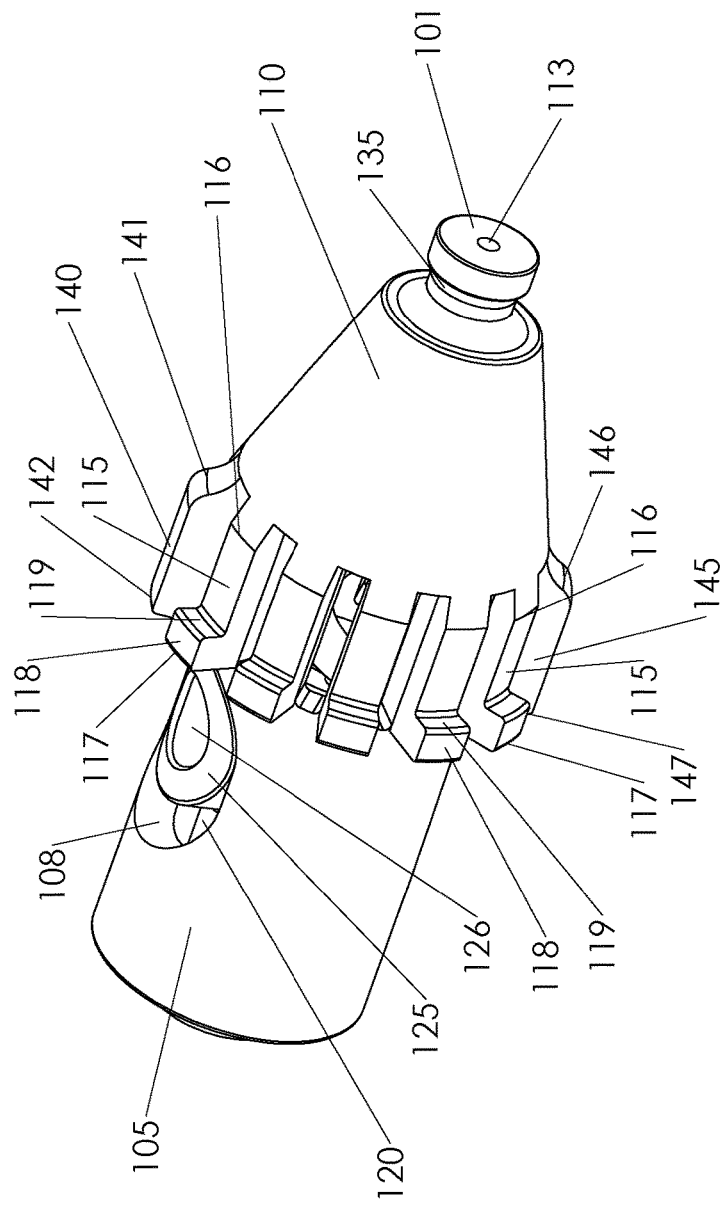
FIGS. 1A, 1B, and 1C are schematic diagrams illustrating a transitory element.
Figure 1B:
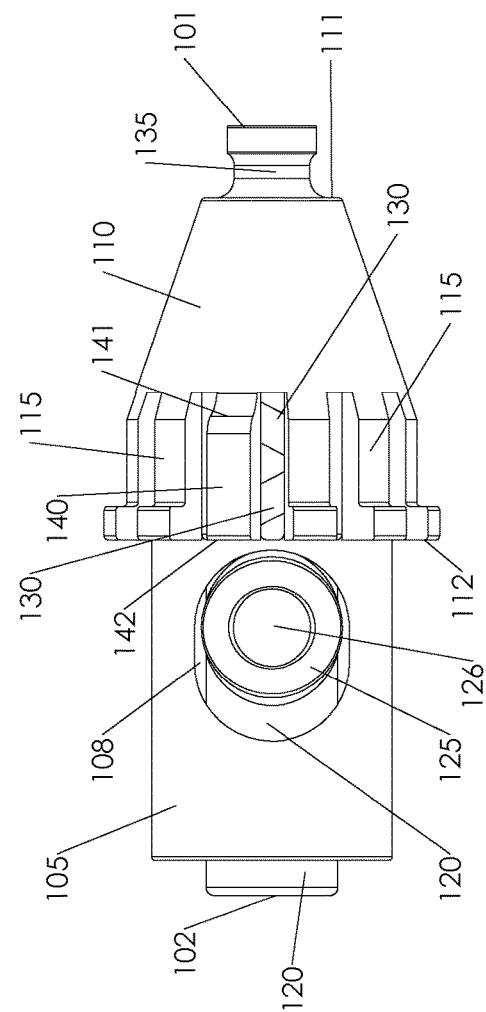
Figure 1C:
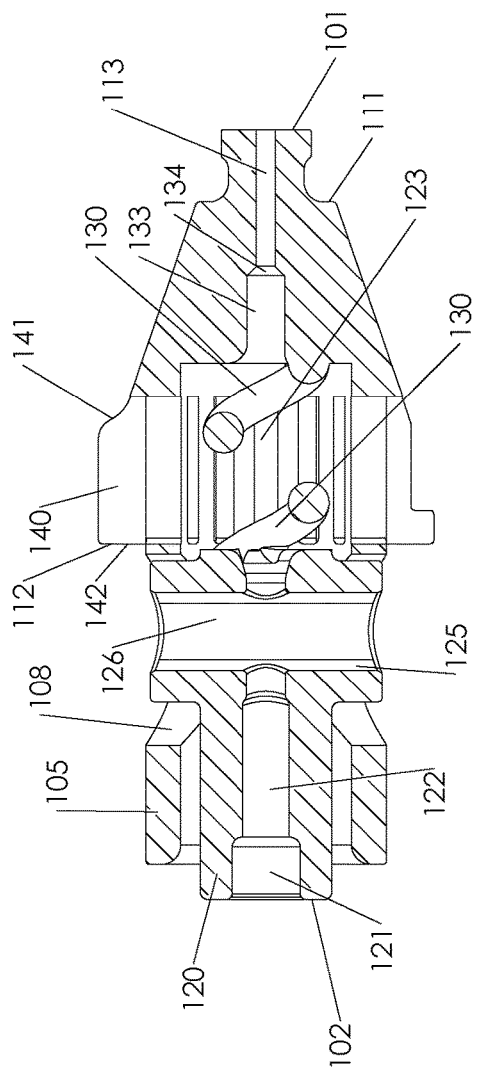

FIGS. 1A, 1B, and 1C are schematic diagrams illustrating a transitory element 100. FIG. 1A illustrates an isometric view of a transitory element 100. FIG. 1B illustrates a superior view of a transitory element 100. FIG. 1C illustrates a cross-sectional view in a sagittal plane of a transitory element 100. In one or more embodiments, a transitory element 100 may comprise a transitory element distal end 101 and a transitory element proximal end 102. Illustratively, transitory element 100 may comprise an outer base 105, a nosecone 110, and a fixation mechanism distal receptacle 120. In one or more embodiments, outer base 105 may comprise an outer base aperture 108. Illustratively, nosecone 110 may comprise a nosecone distal end 111 and a nosecone proximal end 112. In one or more embodiments, nosecone 110 may comprise a hypodermic tube housing 113 and a plurality of radial projections 115. Illustratively, each radial projection 115 of the plurality of radial projections 115 may comprise a radial projection distal end 116 and a radial projection proximal end 117. In one or more embodiments, each radial projection 115 of the plurality of radial projections 115 may be separated from at least one radial projection 115 of the plurality of radial projections 115 by an aperture. Illustratively, nosecone 110 may comprise a plurality of apertures. In one or more embodiments, each radial projection 115 of the plurality of radial projections 115 may comprise a tip cover buttress 118 and a tip cover proximal end interface 119. Illustratively, transitory element 100 may comprise a fixation mechanism support 125 and a fixation mechanism housing 126. In one or more embodiments, transitory element 100 may comprise a fixation mechanism distal receptacle 120. Illustratively, transitory element 100 may comprise an identification ring housing 135. In one or more embodiments, transitory element 100 may comprise a superior projection 140 having a superior projection distal end 141 and a superior projection proximal end 142. Illustratively, transitory element 100 may comprise an inferior projection 145 having an inferior projection distal end 146 and an inferior projection proximal end 147.

In one or more embodiments, transitory element 100 may comprise a fixation mechanism distal housing 121, an inner lumen 122, an inner bore 123, a pressure mechanism 130, a nosecone inner bore 133, and a nosecone inner bore distal taper 134. In one or more embodiments, pressure mechanism 130 may be disposed between inner lumen 122 and hypodermic tube housing 113. Illustratively, inner bore 123 may be disposed in pressure mechanism 130. In one or more embodiments, a portion of pressure mechanism 130 may be disposed in the plurality of radial projections 115. In one or more embodiments, pressure mechanism 130 may be configured to provide a force. Illustratively, pressure mechanism 130 may be configured to provide a constant or uniform force. In one or more embodiments, pressure mechanism 130 may be configured to provide a variable force. Illustratively, pressure mechanism 130 may comprise a spring or a coil. In one or more embodiments, pressure mechanism 130 may comprise a spring having a spring constant in a range of 65.0 to 125.0 pounds per inch, e.g., pressure mechanism 130 may comprise a spring having a spring constant of 94.7 pounds per inch. Illustratively, pressure mechanism 130 may comprise a spring having a spring constant of less than 65.0 pounds per inch or greater than 125.0 pounds per inch. In one or more embodiments, pressure mechanism 130 may comprise a spring having a spring constant in a range of 77.5 to 133.0 pounds per inch, e.g., pressure mechanism 130 may comprise a spring having a spring constant of 107.4 pounds per inch. Illustratively, pressure mechanism 130 may comprise a spring having a spring constant of less than 77.5 pounds per inch or greater than 133.0 pounds per inch. In one or more embodiments, pressure mechanism 130 may comprise a pneumatic system. Illustratively, fixation mechanism support 125 may be disposed in outer base aperture 108, e.g., fixation mechanism support 125 may be configured to actuate within outer base aperture 108. In one or more embodiments, pressure mechanism 130 may be configured to provide a force that resists an actuation of fixation mechanism support 125 within outer base aperture 108. Illustratively, pressure mechanism 130 may be configured to provide a force that facilitates an actuation of fixation mechanism support 125 within outer base aperture 108. In one or more embodiments, nosecone inner bore distal taper 134 may be disposed between nosecone inner bore 133 and hypodermic tube housing 113. Illustratively, nosecone inner bore 133 may be disposed between nosecone inner bore distal taper 134 and inner bore 123.

In one or more embodiments, fixation mechanism distal receptacle 120 may be configured to extend a distance from outer base 105. Illustratively, fixation mechanism distal receptacle 120 may be configured to extend a distance from outer base 105 in a range of 0.02 to 0.06 inches, e.g., fixation mechanism distal receptacle 120 may be configured to extend a distance from outer base 105 of 0.045 inches. In one or more embodiments, fixation mechanism distal receptacle 120 may be configured to extend a distance from outer base 105 of less than 0.02 inches or greater than 0.06 inches. Illustratively, fixation mechanism distal housing 121 may be disposed in fixation mechanism distal receptacle 120. In one or more embodiments, inner lumen 122 may be disposed between fixation mechanism distal housing 121 and pressure mechanism 130. Illustratively, hypodermic tube housing 113 may be disposed between inner bore 123 and nosecone distal end 111.

In one or more embodiments, transitory element 100 may be manufactured from a material configured to deform if transitory element 100 is sterilized in a medical autoclave, e.g., transitory element 100 may be manufactured from a material configured to permanently deform if transitory element 100 is sterilized in a medical autoclave. Illustratively, transitory element 100 may be manufactured from a material having a melting point below a temperature parameter for a steam sterilization cycle, e.g., transitory element 100 may be manufactured from a material having a melting point below a temperature parameter for a gravity-displacement steam sterilization cycle, a dynamic-air-removal steam sterilization cycle, etc. In one or more embodiments, transitory element 100 may be manufactured from a material having a melting point below 140.0 degrees Fahrenheit. Illustratively, transitory element 100 may be manufactured from a material having a melting point in a range of 158.0 to 212.0 degrees Fahrenheit, e.g., transitory element 100 may be manufactured from a material having a melting point of 160.0 degrees Fahrenheit. In one or more embodiments, transitory element 100 may be manufactured from a material having a melting point of less than 158.0 degrees Fahrenheit or greater than 212.0 degrees Fahrenheit. In one or more embodiments, transitory element 100 may be manufactured from a material having a melting point below 250.0 degrees Fahrenheit. Illustratively, transitory element 100 may be manufactured from a material having a melting point below 270.0 degrees Fahrenheit. In one or more embodiments, transitory element 100 may be manufactured from a material having a melting point below 275.0 degrees Fahrenheit.

Illustratively, transitory element 100 may be manufactured from a material configured to temporarily deform if transitory element 100 is sterilized in a medical autoclave, e.g., transitory element 100 may be manufactured from a material configured to absorb water in a medical autoclave. In one or more embodiments, an absorption of water may be configured to deform transitory element 100, e.g., an absorption of water may be configured to cause transitory element 100 to expand. Illustratively, transitory element 100 may be manufactured from a porous material configured to facilitate a deformation of transitory element 100 if transitory element 100 is sterilized in a medical autoclave. In one or more embodiments, transitory element 100 may be manufactured with one or more cavities configured to facilitate a deformation of transitory element 100 if transitory element 100 is sterilized in a medical autoclave. Illustratively, transitory element 100 may be manufactured from any suitable material, e.g., polymers, metals, metal alloys, etc., or from any combination of suitable materials. In one or more embodiments, transitory element 100 may be manufactured by a 3D printing process. For example, transitory element 100 may be manufactured by selective laser sintering, selective heat sintering, selective laser melting, electron-beam melting, direct metal laser sintering, electron beam freeform fabrication, etc. Illustratively, transitory element 100 may be manufactured by injection molding. In one or more embodiments, transitory element 100 may be manufactured by an addi-tive manufacturing process.

In one or more embodiments, transitory element 100 may be manufactured from poly(acrylamide), poly(acrylic acid), poly(adipic anhydride), poly(7-aminoenanthic acid), poly (12-aminolauric acid), poly(11-aminoundecanoic acid), poly (azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4- cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)-caproate], poly[ethylene p-(carboxyphenoxy)-heptanoate], poly[ethylene p-(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene disiloxanylenedipropionamide), poly[(ethylenedithio)-diacetic anhydride], poly[(ethylenedithio)-dipropionic anhydride], poly(ethylene dithionisophthalate), poly(ethelene dithiotetramethylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc. Illustratively, transitory element 100 may be manufactured from any substituted polymers of poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)-caproate], poly[ethylene p-(carboxyphenoxy)-heptanoate], poly[ethylene p-(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene disiloxanylenedipropionamide), poly[(ethylenedithio)-diacetic anhydride], poly[(ethylenedithio)dipropionic anhydride], poly(ethylene dithionisophthalate), poly(ethelene dithiotetramethylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)-dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc.

In one or more embodiments, transitory element 100 may be manufactured by an additive manufacturing process, e.g., transitory element 100 may be manufactured by an additive manufacturing process to eliminate at least one component but retain a functionality of the at least one component. Illustratively, transitory element 100 may be manufactured by an additive manufacturing process to eliminate a spring component but retain the spring component functionality, e.g., pressure mechanism 130 may be configured to retain the spring component functionality. In one or more embodiments, transitory element 100 may be manufactured by an additive manufacturing process to eliminate a lock component but retain the lock component functionality, e.g., fixation mechanism support 125 and fixation mechanism housing 126 may be configured to retain the lock component functionality. Illustratively, transitory element 100 may be manufactured by an additive manufacturing process to eliminate a plurality of components but retain a functionality of component of the plurality of components. In one or more embodiments, transitory element 100 may be manufactured by an additive manufacturing process to eliminate a spring component and a lock component but retain the spring component functionality and the lock component functionality, e.g., pressure mechanism 130 may be configured to retain the spring component functionality and fixation mechanism support 125 and fixation mechanism housing 126 may be configured to retain the lock component functionality. Illustratively, transitory element 100 may be manufactured by an additive manufacturing process to eliminate one or more components wherein eliminating one or more components reduces a cost to manufacture transitory element 100.

Figure 2:
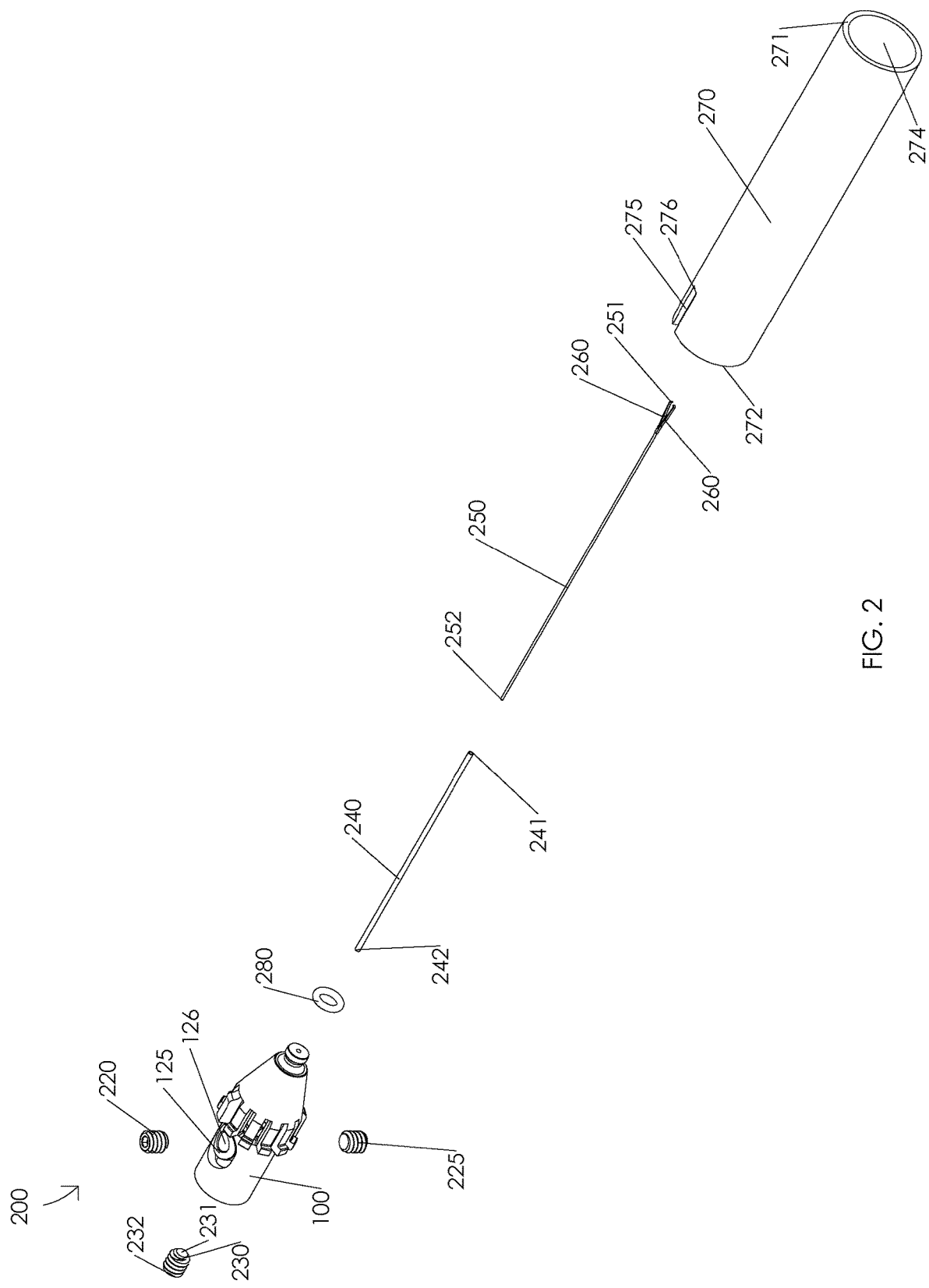
FIG. 2 is a schematic diagram illustrating an exploded view of an instrument tip assembly.

FIG. 2 is a schematic diagram illustrating an exploded view of an instrument tip assembly 200. Illustratively, an instrument tip assembly 200 may comprise a transitory element 100, a superior fixation mechanism 220, an inferior fixation mechanism 225, a fixation mechanism 230, a hypodermic tube 240, a blank 250, a tip cover 270, and an identification ring 280. In one or more embodiments, superior fixation mechanism 220 may comprise a setscrew, a magnet, an adhesive, a weld, etc. Illustratively, inferior fixation mechanism 225 may comprise a setscrew, a magnet, an adhesive, a weld, etc. In one or more embodiments, fixation mechanism 230 may comprise a fixation mechanism distal end 231 and a fixation mechanism proximal end 232. Illustratively, fixation mechanism 230 may comprise a setscrew, a magnet, an adhesive, a weld, etc. In one or more embodiments, hypodermic tube 240 may comprise a hypodermic tube distal end 241 and a hypodermic tube proximal end 242. Illustratively, blank 250 may comprise a blank distal end 251 and a blank proximal end 252. In one or more embodiments, blank 250 may comprise one or more instrument jaws 260, e.g., blank 250 may comprise a pair of instrument jaws 260. Illustratively, blank 250 may comprise a plurality of instrument jaws 260, e.g., blank 250 may comprise two instrument jaws 260, three instrument jaws 260, four instrument jaws 260, five instrument jaws 260, six instrument jaws 260, etc. In one or more embodiments, instrument jaws 260 may comprise forceps jaws. Illustratively, instrument jaws 260 may comprise scissors jaws. Illustratively, tip cover 270 may comprise a tip cover distal end 271 and a tip cover proximal end 272. In one or more embodiments, tip cover 270 may comprise a tip cover inner bore 274. Illustratively, tip cover 270 may comprise a first alignment aperture 275 having a first alignment aperture distal end 276 and a second alignment aperture 275 having a second alignment aperture distal end 276.

Figure 3C:
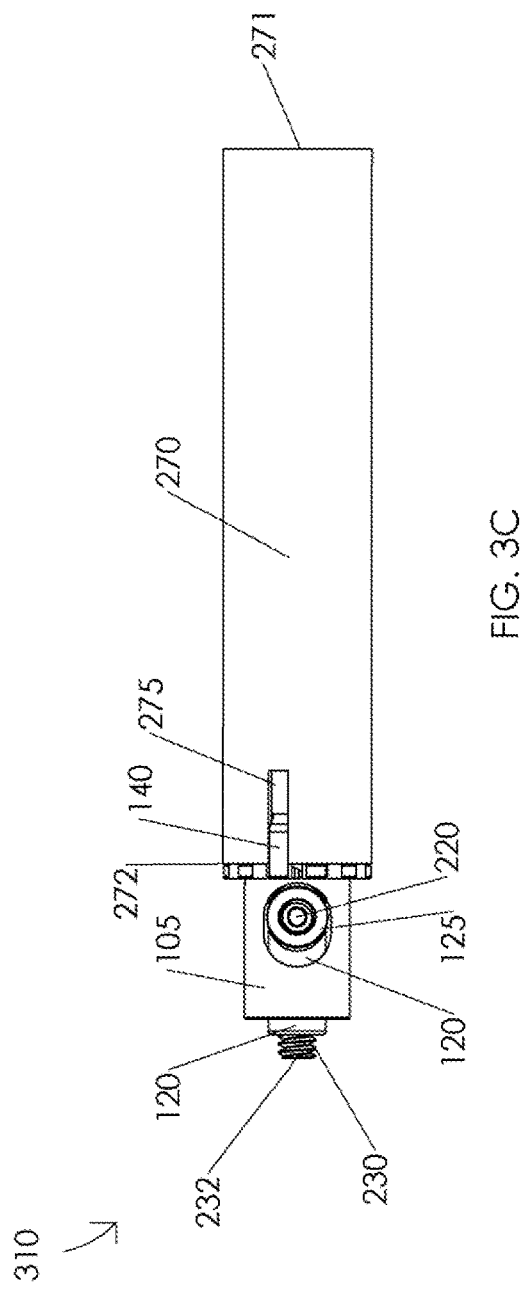
Figure 3D:
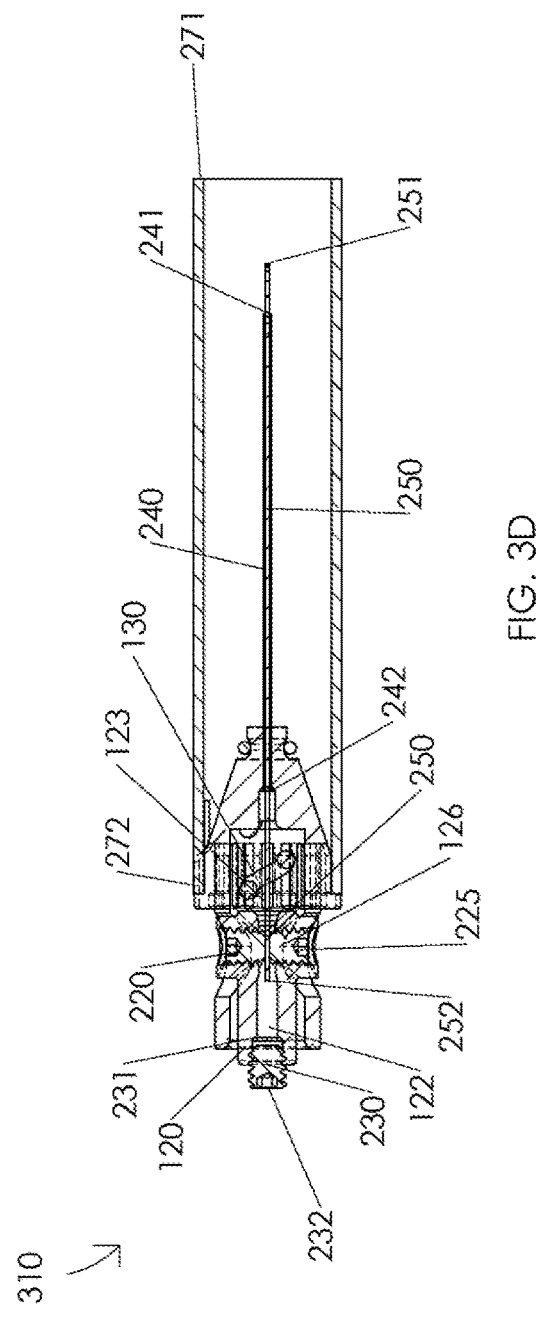

FIGS. 3A, 3B, 3C, and 3D are schematic diagrams illustrating an assembled instrument tip 300. FIG. 3A illustrates a superior view of an assembled instrument tip 300. FIG. 3B illustrates a cross-sectional view in a sagittal plane of an assembled instrument tip 300. FIG. 3C illustrates a superior view of an assembled instrument tip with covered tip 310. FIG. 3D illustrates a cross-sectional view in a sagittal plane of an assembled instrument tip with covered tip 310. Illustratively, a portion of hypodermic tube 240 may be disposed in a portion of nosecone 110, e.g., hypodermic tube proximal end 242 may be disposed in a portion of nosecone 110. In one or more embodiments, a portion of hypodermic tube 240 may be fixed within a portion of nosecone 110, e.g., a portion of hypodermic tube 240 may be fixed within a portion of nosecone 110 by an interference fit, an adhesive, a setscrew, a weld, etc. Illustratively, a portion of hypodermic tube 240 may be disposed in hypodermic tube housing 113, e.g., hypodermic tube proximal end 242 may be disposed in hypodermic tube housing 113 wherein hypodermic tube distal end 241 extends from transitory element distal end 101. In one or more embodiments, a portion of hypodermic tube 240 may be fixed within hypodermic tube housing 113, e.g., a portion of hypodermic tube 240 may be fixed within hypodermic tube housing 113 by an interference fit, an adhesive, a setscrew, a weld, etc.

Illustratively, blank 250 may be disposed in hypodermic tube 240, e.g., blank 250 may be disposed in hypodermic tube 240 wherein blank distal end 251 extends from hypodermic tube distal end 241. In one or more embodiments, blank 250 may be disposed in hypodermic tube 240, nosecone 110, hypodermic tube housing 113, nosecone inner bore distal taper 134, nosecone inner bore 133, inner bore 123, pressure mechanism 130, and fixation mechanism housing 126. Illustratively, superior fixation mechanism 220 may be disposed in fixation mechanism housing 126. In one or more embodiments, inferior fixation mechanism 225 may be disposed in fixation mechanism housing 126. Illustratively, a portion of blank 250 may be disposed between superior fixation mechanism 220 and inferior fixation mechanism 225 within fixation mechanism housing 126. In one or more embodiments, superior fixation mechanism 220 and inferior fixation mechanism 225 may be configured to fix a portion of blank 250 within fixation mechanism housing 126. For example, superior fixation mechanism 220 may comprise a first setscrew and inferior fixation mechanism 225 may comprise a second setscrew. Illustratively, a portion of blank 250 may be fixed in fixation mechanism housing 126 by an interference fit, an adhesive, a setscrew, a weld, etc.

In one or more embodiments, a portion of fixation mechanism 230 may be disposed in fixation mechanism distal receptacle 120, e.g., fixation mechanism distal end 231 may be disposed in fixation mechanism distal receptacle 120. Illustratively, a first portion of fixation mechanism 230 may be disposed in fixation mechanism distal receptacle 120 wherein a second portion of fixation mechanism 230 extends from transitory element proximal end 102, e.g., fixation mechanism distal end 231 may be disposed in fixation mechanism distal receptacle 120 wherein fixation mechanism proximal end 232 extends from transitory element proximal end 102. In one or more embodiments, a portion of fixation mechanism 230 may be disposed in fixation mechanism distal housing 121. Illustratively, fixation mechanism distal end 231 may be disposed in fixation mechanism distal housing 121 wherein fixation mechanism proximal end 232 extends from transitory element proximal end 102. In one or more embodiments, fixation mechanism distal end 231 may be disposed in fixation mechanism distal housing 121 wherein fixation mechanism proximal end 232 extends a distance from transitory element proximal end 102 in a range of 0.065 to 0.125 inches, e.g., fixation mechanism distal end 231 may be disposed in fixation mechanism distal housing 121 wherein fixation mechanism proximal end 232 extends a distance from transitory element proximal end 102 of 0.094 inches. Illustratively, fixation mechanism distal end 231 may be disposed in fixation mechanism distal housing 121 wherein fixation mechanism proximal end 232 extends a distance from transitory element proximal end 102 of less than 0.065 inches or greater than 0.125 inches. In one or more embodiments, a portion of fixation mechanism 230 may be fixed in fixation mechanism distal housing 121, e.g., fixation mechanism distal end 231 may be fixed in fixation mechanism distal housing 121. Illustratively, a portion of fixation mechanism 230 may be fixed in fixation mechanism distal housing 121 by an interference fit, an adhesive, a magnetic field, a weld, a threading, etc.

In one or more embodiments, identification ring 280 may be disposed over identification ring housing 135, e.g., identification ring 280 may be fixed in identification ring housing 135. Illustratively, identification ring 280 may be configured to indicate one or more properties of assembled instrument tip 300 to a user, e.g., identification ring 280 may be configured to visually indicate one or more properties of assembled instrument tip 300 to a user. In one or more embodiments, identification ring 280 may be configured to indicate a type of cannula that is compatible with assembled instrument tip 300 to a user, e.g., identification ring 280 may be configured to visually indicate a type of cannula that is compatible with assembled instrument tip 300 to a user. Illustratively, identification ring 280 may be configured to indicate a size of cannula that is compatible with assembled instrument tip 300 to a user, e.g., identification ring 280 may be configured to visually indicate a size of cannula that is compatible with assembled instrument tip 300 to a user.

In one or more embodiments, tip cover 270 may be disposed over a portion of transitory element 100 when assembled instrument tip 300 comprises an assembled instrument tip with covered tip 310. Illustratively, tip cover 270 may be disposed over a portion of nosecone 110 when assembled instrument tip 300 comprises an assembled instrument tip with covered tip 310, e.g., tip cover 270 may be disposed over nosecone distal end 111 when assembled instrument tip 300 comprises an assembled instrument tip with covered tip 310. In one or more embodiments, a portion of nosecone 110 may be disposed in tip cover inner bore 274 when assembled instrument tip 300 comprises an assembled instrument tip with covered tip 310, e.g., nosecone distal end 111 may be disco posed in tip cover inner bore 274 when assembled instrument tip 300 comprises an assembled instrument tip with covered tip 310. Illustratively, tip cover 270 may be disposed over hypodermic tube 240 when assembled instrument tip 300 comprises an assembled instrument tip with covered tip 310, e.g., tip cover 270 may be disposed over hypodermic tube 240 wherein hypodermic tube distal end 241 is disposed between tip cover distal end 271 and tip cover proximal end 272 and wherein hypodermic tube proximal end 242 is disposed between tip cover distal end 271 and tip cover proximal end 272 when assembled instrument tip 300 comprises an assembled instrument tip with covered tip 310. In one or more embodiments, hypodermic tube 240 may be disposed in tip cover inner bore 274 when assembled instrument tip 300 comprises an assembled instrument tip with covered tip 310, e.g., hypodermic tube 240 may be disposed in tip cover inner bore 274 wherein hypodermic tube distal end 241 is disposed in tip cover inner bore 274 and hypodermic tube proximal end 242 is disposed in tip cover inner bore 274 when assembled instrument tip 300 comprises an assembled instrument tip with covered tip 310. Illustratively, tip cover 270 may be disposed over a portion of blank 250 when assembled instrument tip 300 comprises an assembled instrument tip with covered tip 310, e.g., tip cover 270 may be disposed over blank distal end 251 when assembled instrument tip 300 comprises an assembled instrument tip with covered tip 310. In one or more embodiments, a portion of blank 250 may be disposed in tip cover inner bore 274 when assembled instrument tip 300 comprises an assembled instrument tip with covered tip 310, e.g., blank distal end 251 may be disposed in tip cover inner bore 274 when assembled instrument tip 300 comprises an assembled instrument tip with covered tip 310.

Illustratively, superior projection 140 may be disposed in first alignment aperture 275 when assembled instrument tip 300 comprises an assembled instrument tip with covered tip 310. In one or more embodiments, inferior projection 145 may be disposed in second alignment aperture 275 when assembled instrument tip 300 comprises an assembled instrument tip with covered tip 310. Illustratively, tip cover 270 may be disposed over a portion of radial projection 115 when assembled instrument tip 300 comprises an assembled instrument tip with covered tip 310, e.g., tip cover 270 may be disposed over radial projection distal end 116 when assembled instrument tip 300 comprises an assembled instrument tip with covered tip 310. In one or more embodiments, tip cover 270 may be disposed over a portion of each radial projection 115 of a plurality of radial projections 115 when assembled instrument tip 300 comprises an assembled instrument tip with covered tip 310, e.g., tip cover 270 may be disposed over each radial projection distal end 116 of a plurality of radial projection distal ends 116 when assembled instrument tip 300 comprises an assembled instrument tip with covered tip 310. Illustratively, a portion of radial projection 115 may be disposed in tip cover inner bore 274 when assembled instrument tip 300 comprises an assembled instrument tip with covered tip 310, e.g., radial projection distal end 116 may be disposed in tip cover inner bore 274 when assembled instrument tip 300 comprises an assembled instrument tip with covered tip 310. In one or more embodiments, a portion of each radial projection 115 of a plurality of radial projections 115 may be disposed in tip cover inner bore 274 when assembled instrument tip 300 comprises an assembled instrument tip with covered tip 310, e.g., each radial projection distal end 116 of a plurality of radial projection distal ends 116 may be disposed in tip cover inner bore 274 when assembled instrument tip 300 comprises an assembled instrument tip with covered tip 310.

Illustratively, tip cover proximal end 272 may be adjacent to tip cover proximal end interface 119 when assembled instrument tip 300 comprises an assembled instrument tip with covered tip 310, e.g., tip cover proximal end 272 may abut tip cover proximal end interface 119 when assembled instrument tip 300 comprises an assembled instrument tip with covered tip 310. In one or more embodiments, tip cover proximal end 272 may be adjacent to each tip cover proximal end interface 119 of a plurality of tip cover proximal end interfaces 119 when assembled instrument tip 300 comprises an assembled instrument tip with covered tip 310, e.g., tip cover proximal end 272 may abut each tip cover proximal end interface 119 of a plurality of tip cover proximal end interfaces 119 when assembled instrument tip 300 comprises an assembled instrument tip with covered tip 310. Illustratively, tip cover 270 may be configured to prevent damage to a portion of assembled instrument tip 300 when assembled instrument tip 300 comprises an assembled instrument tip with covered tip 310, e.g., tip cover 270 may be configured to prevent damage to a portion of hypodermic tube 240 when assembled instrument tip 300 comprises an assembled instrument tip with covered tip 310. In one or more embodiments, tip cover 270 may be configured to prevent damage to a portion of blank 250 when assembled instrument tip 300 comprises an assembled instrument tip with covered tip 310, e.g., tip cover 270 may be configured to prevent damage to instrument jaw 260 when assembled instrument tip 300 comprises an assembled instrument tip with covered tip 310.

In one or more embodiments, assembled instrument tip 300 may be a single-use instrument, e.g., assembled instrument tip 300 may be intended for only one use in a surgery. Illustratively, assembled instrument tip 300 may be sterilized after manufacturing but prior to shipment of assembled instrument tip 300 to a user, e.g., assembled instrument tip 300 may be sterilized by ethylene oxide after manufacturing but prior to shipment of assembled instrument tip 300 to a user. In one or more embodiments, one or more properties of assembled instrument tip 300 may be configured to prevent a user from using a sterile assembled instrument tip 300 in a first surgical procedure causing the assembled instrument tip 300 to become non-sterile, sterilizing the assembled instrument tip 300, and using the sterile assembled instrument tip 300 in a second surgical procedure. Illustratively, transitory element 100 may be manufactured from a material configured to deform if transitory element 100 is sterilized in a medical autoclave. In one or more embodiments, transitory element 100 may be manufactured from a material configured to retain ethylene oxide, e.g., transitory element 100 may be manufactured from a material having a degree of crystallinity greater than 60.0 percent. For example, transitory element 100 may be manufactured from a material having a degree of crystallinity greater than 70.0 percent. In one or more embodiments, transitory element 100 may be manufactured from a material having a degree of crystallinity in a range of 60.0 to 80.0 percent, e.g., transitory element 100 may be manufactured from a material having a degree of crystallinity of 75.0 percent. Illustratively, transitory element 100 may be manufactured from a material having a degree of crystallinity of less than 60.0 percent or greater than 80.0 percent. In one or more embodiments, transitory element 100 may be manufactured from a material configured to retain less than 4.0 milligrams of ethylene oxide after a first sterilization by ethylene oxide and configured to retain more than 4.0 milligrams of ethylene oxide after a second sterilization by ethylene oxide. For example, transitory element 100 may be manufactured from polyoxymethylene, polytetrafluoroethylene, isotactic polypropylene, high-density polyethylene, etc. In one or more embodiments, transitory element 100 may be manufactured from a material configured to degrade if transitory element 100 is sterilized by plasma sterilization, e.g., transitory element 100 may be manufactured by a material configured to cross-link in plasma sterilization.

Illustratively, fixation mechanism 230 may be manufactured from a material configured to deform if fixation mechanism 230 is sterilized in a medical autoclave. In one or more embodiments, fixation mechanism 230 may be manufactured from a material having a melting point below 140.0 degrees Fahrenheit. Illustratively, fixation mechanism 230 may be manufactured from a material having a melting point in a range of 158.0 to 212.0 degrees Fahrenheit, e.g., fixation mechanism 230 may be manufactured from a material having a melting point of 160.0 degrees Fahrenheit. In one or more embodiments, fixation mechanism 230 may be manufactured from a material having a melting point of less than 158.0 degrees Fahrenheit or greater than 212.0 degrees Fahrenheit. Illustratively, hypodermic tube 240 may be manufactured from a material configured to deform if hypodermic tube 240 is sterilized in a medical autoclave. In one or more embodiments, hypodermic tube 240 may be manufactured from a material having a melting point below 140.0 degrees Fahrenheit. Illustratively, hypodermic tube 240 may be manufactured from a material having a melting point in a range of 158.0 to 212.0 degrees Fahrenheit, e.g., hypodermic tube 240 may be manufactured from a material having a melting point of 160.0 degrees Fahrenheit. In one or more embodiments, hypodermic tube 240 may be manufactured from a material having a melting point of less than 158.0 degrees Fahrenheit or greater than 212.0 degrees Fahrenheit. Illustratively, blank 250 may be manufactured from a material configured to deform if blank 250 is sterilized in a medical autoclave. In one or more embodiments, blank 250 may be manufactured from a material having a melting point below 140.0 degrees Fahrenheit. Illustratively, blank 250 may be manufactured from a material having a melting point in a range of 158.0 to 212.0 degrees Fahrenheit, e.g., blank 250 may be manufactured from a material having a melting point of 160.0 degrees Fahrenheit. In one or more embodiments, blank 250 may be manufactured from a material having a melting point of less than 158.0 degrees Fahrenheit or greater than 212.0 degrees Fahrenheit.

Figure 4:
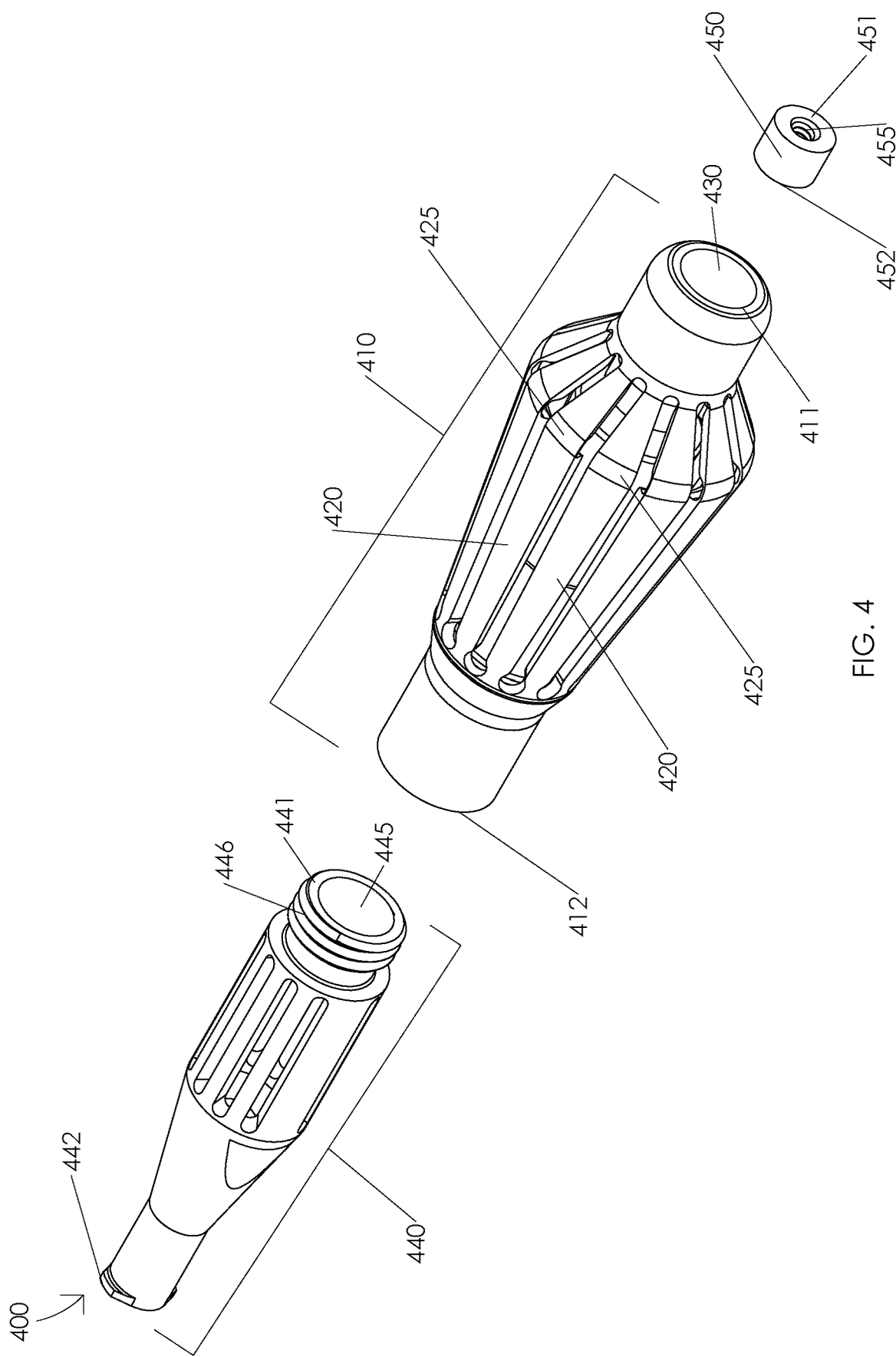
FIG. 4 is a schematic diagram illustrating an exploded view of an instrument handle assembly.

FIG. 4 is a schematic diagram illustrating an exploded view of an instrument handle assembly 400. Illustratively, an instrument handle assembly 400 may comprise an actuation structure 410, a handle base 440, and a fixation mechanism proximal receptacle 450. In one or more embodiments, an actuation structure 410 may comprise an actuation structure distal end 411 and an actuation structure proximal end 412. Illustratively, actuation structure 410 may comprise an instrument tip housing 430. In one or more embodiments, instrument tip housing 430 may be configured to house assembled instrument tip 300. Illustratively, actuation structure 410 may comprise a plurality of actuation arms 420. In one or more embodiments, each actuation arm 420 may comprise at least one extension joint 425. In one or more embodiments, actuation structure 410 may comprise a shape memory material configured to project actuation structure distal end 411 a first distance from actuation structure proximal end 412, e.g., when actuation structure 410 is fully decompressed. Illustratively, actuation structure 410 may comprise a shape memory material configured to project actuation structure distal end 411 a second distance from actuation structure proximal end 412, e.g., when actuation structure 410 is fully compressed. In one or more embodiments, the second distance from actuation structure proximal end 412 may be greater than the first distance from actuation structure proximal end 412. Actuation structure 410 may be manufactured from any suitable material, e.g., polymers, metals, metal alloys, etc., or from any combination of suitable materials. Illustratively, actuation structure 410 may be compressed by an application of a compressive force to actuation structure 410. In one or more embodiments, actuation structure 410 may be compressed by an application of one or more compressive forces located at one or more locations around an outer perimeter of actuation structure 410. Illustratively, the one or more locations may comprise any of a plurality of locations around the outer perimeter of actuation structure 410. For example, a surgeon may compress actuation structure 410 by squeezing actuation structure 410. Illustratively, the surgeon may compress actuation structure 410 by squeezing actuation structure 410 at any particular location of a plurality of locations around an outer perimeter of actuation structure 410. In one or more embodiments, actuation structure 410 may be compressed by an application of a compressive force to any one or more of the plurality of actuation arms 420. Illustratively, each actuation arm 420 may be configured to actuate independently. In one or more embodiments, each actuation arm 420 may be connected to one or more of the plurality of actuation arms 420 wherein an actuation of a particular actuation arm 420 may be configured to actuate every actuation arm 420 of the plurality of actuation arms 420. Illustratively, one or more actuation arms 420 may be configured to actuate in pairs or groups. For example, an actuation of a first actuation arm 420 may be configured to actuate a second actuation arm 420. In one or more embodiments, a compression of actuation structure 410, e.g., due to an application of a compressive force to a particular actuation arm 420, may be configured to actuate the particular actuation arm 420. Illustratively, an actuation of the particular actuation arm 420 may be configured to actuate every actuation arm 420 of the plurality of actuation arms 420. In one or more embodiments, an application of a compressive force to a particular actuation arm 420 may be configured to extend at least one extension joint 425 of the particular actuation arm 420.

Illustratively, handle base 440 may comprise a handle base distal end 441 and a handle base proximal end 442. In one or more embodiments, handle base 440 may comprise a handle base inner lumen 445. Illustratively, handle base 440 may comprise a handle base thread 446 configured to interface with a portion of actuation structure 410. In one or more embodiments, fixation mechanism proximal receptacle 450 may comprise a fixation mechanism proximal receptacle distal end 451 and a fixation mechanism proximal receptacle proximal end 452. Illustratively, fixation mechanism proximal receptacle 450 may comprise a fixation mechanism proximal housing 455. In one or more embodiments, fixation mechanism proximal housing 455 may be configured to house a portion of fixation mechanism 230, e.g., fixation mechanism proximal housing 455 may be configured to house fixation mechanism proximal end 232.

Figure 5:
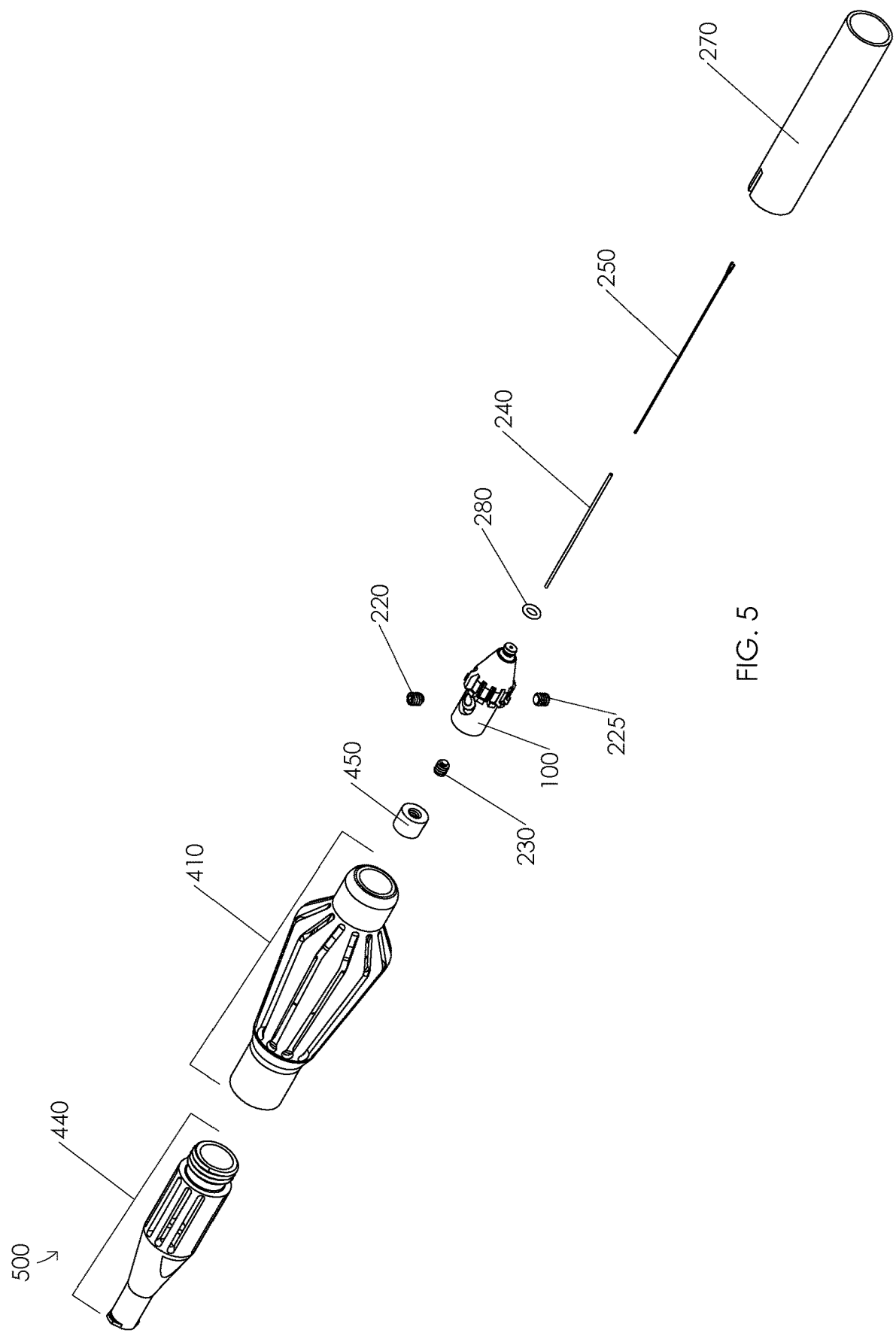
FIG. 5 is a schematic diagram illustrating an exploded view of an instrument assembly.

FIG. 5 is a schematic diagram illustrating an exploded view of an instrument assembly 500. In one or more embodiments, an instrument assemble 500 may comprise a handle base 440, an actuation structure 410, a fixation mechanism proximal receptacle 450, a fixation mechanism 230, a transitory element 100, a superior fixation mechanism 220, an inferior fixation mechanism 225, an identification ring 280, a hypodermic tube 240, a blank 250, and a tip cover 270.

Figure 6A:
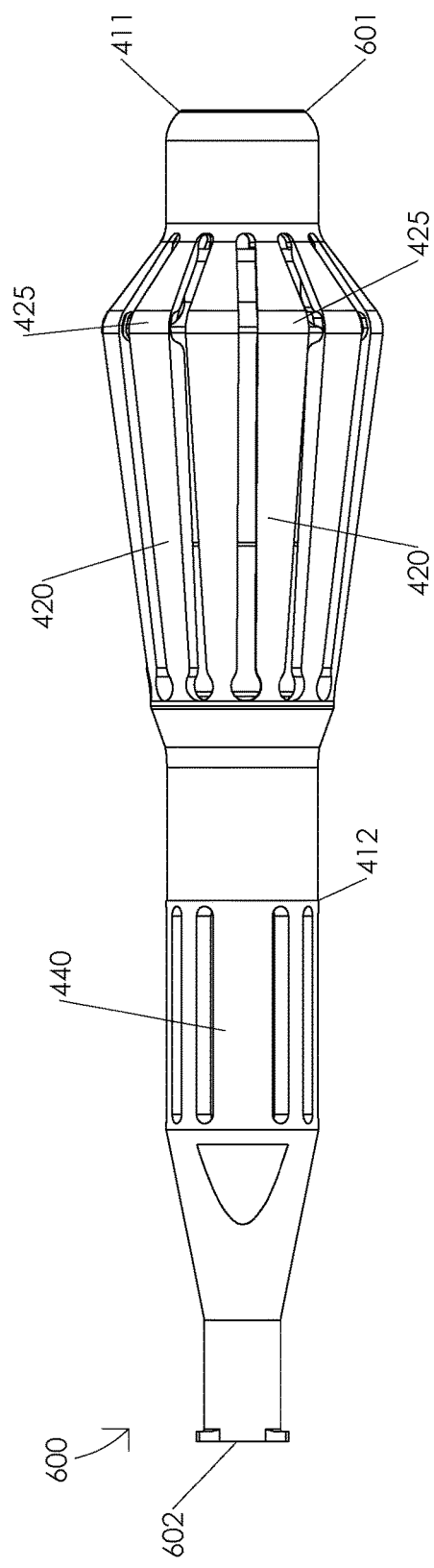
FIGS. 6A and 6B are schematic diagrams illustrating an assembled instrument handle.
Figure 6B:
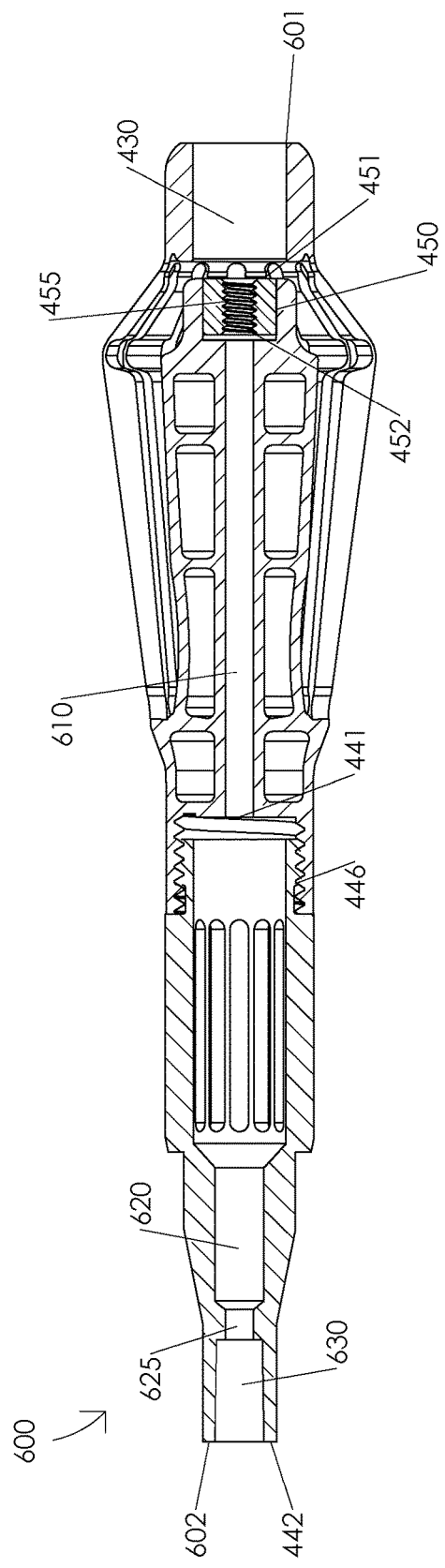

FIGS. 6A and 6B are schematic diagrams illustrating an assembled instrument handle 600. FIG. 6A illustrates a superior view of an assembled instrument handle 600. FIG. 6B illustrates a cross-sectional view in a sagittal plane of an assembled instrument handle 600. Illustratively, assembled instrument handle 600 may comprise an assembled instrument handle distal end 601 and an assembled instrument handle proximal end 602. In one or more embodiments, assembled instrument handle 600 may comprise a handle inner lumen 610, a handle base distal inner bore 620, a handle base inner lumen 625, and a handle base proximal inner bore 630. Illustratively, a portion of handle base 440 may be disposed in a portion of actuation structure 410, e.g., handle base distal end 441 may be disposed in actuation structure proximal end 412. Illustratively, a portion of handle base 440 may be disposed in a portion of actuation structure 410 wherein handle base inner lumen 445 is oriented to align with handle inner lumen 610. In one or more embodiments, a portion of handle base 440 may be disposed in actuation structure 410 wherein handle base proximal end 442 is assembled instrument handle proximal end 602. Illustratively, a portion of handle base 440 may be fixed in a portion of actuation structure 410, e.g., a portion of handle base 440 may be fixed in a portion of actuation structure 410 by an interference fit, an adhesive, a magnetic field, a weld, a threading, etc.

In one or more embodiments, fixation mechanism proximal receptacle 450 may be disposed in actuation structure 410, e.g., fixation mechanism proximal receptacle 450 may be disposed in actuation structure 410 wherein fixation mechanism proximal receptacle distal end 451 is disposed in actuation structure 410 and fixation mechanism proximal receptacle proximal end 452 is disposed in actuation structure 410. Illustratively, fixation mechanism proximal receptacle 450 may be disposed in actuation structure 410 wherein fixation mechanism proximal receptacle 450 is disposed between handle inner lumen 610 and instrument tip housing 430. In one or more embodiments, fixation mechanism proximal receptacle 450 may be disposed in actuation structure 410 wherein fixation mechanism proximal receptacle distal end 451 may be adjacent to a portion of instrument tip housing 430. Illustratively, fixation mechanism proximal receptacle 450 may be disposed in actuation structure 410 wherein fixation mechanism proximal receptacle proximal end 452 may be adjacent to a portion of handle inner lumen 610. In one or more embodiments, fixation mechanism proximal receptacle 450 may be fixed in actuation structure 410, e.g., fixation mechanism proximal receptacle 450 may be fixed in actuation structure 410 by an interference fit, an adhesive, a magnetic field, a weld, a threading, etc. In one or more embodiments, assembled instrument handle 600 may be manufactured from a material suitable for sterilization by a medical autoclave. Illustratively, assembled instrument handle 600 may be manufactured from a material, e.g., Nylon, configured to withstand exposure to temperatures, pressures, and ambient conditions present in a medical autoclave without degradation. For example, assembled instrument handle 600 may be configured to function normally after exposure in a temperature 275 degrees Fahrenheit. In one or more embodiments, assembled instrument handle 600 may be configured to be used in a surgical procedure and then sterilized by a medical autoclave at least three times. Illustratively, assembled instrument handle 600 may be configured to be used in a surgical procedure and then sterilized by a medical autoclave more than three times. In one or more embodiments, assembled instrument handle 600 may be configured to be used in a surgical procedure and then sterilized by a medical autoclave at least nine times. Illustratively, assembled instrument handle 600 may be configured to be used in a surgical procedure and then sterilized by a medical autoclave more than nine times.

FIGS. 7A and 7B are schematic diagrams illustrating an assembled instrument 700. FIG. 7A illustrates a superior view of an assembled instrument 700. FIG. 7B illustrates a cross-sectional view in a sagittal plane of an assembled instrument 700. In one or more embodiments, a portion of fixation mechanism 230 may be disposed in fixation mechanism proximal receptacle 450, e.g., fixation mechanism proximal end 232 may be disposed in fixation mechanism proximal receptacle 450. Illustratively, a first portion of fixation mechanism 230 may be disposed in fixation mechanism proximal receptacle 450 wherein a second portion of fixation mechanism 230 may be disposed in fixation mechanism distal receptacle 120, e.g., fixation mechanism proximal end 232 may be disposed in fixation mechanism proximal receptacle 450 and fixation mechanism distal end 231 may be disposed in fixation mechanism distal receptacle 120. In one or more embodiments, a portion of fixation mechanism 230 may be disposed in fixation mechanism proximal housing 455, e.g., fixation mechanism proximal end 232 may be disposed in fixation mechanism proximal housing 455. Illustratively, a first portion of fixation mechanism 230 may be disposed in fixation mechanism proximal housing 455 wherein a second portion of fixation mechanism 230 may be disposed in fixation mechanism distal housing 121, e.g., fixation mechanism proximal end 232 may be disposed in fixation mechanism proximal housing 455 and fixation mechanism distal end 321 may be disposed in fixation mechanism distal housing 121. In one or more embodiments, a portion of fixation mechanism 230 may be fixed in fixation mechanism proximal housing 455, e.g., fixation mechanism proximal end 232 may be fixed in fixation mechanism proximal housing 455. Illustratively, a portion of fixation mechanism 230 may be fixed in fixation mechanism proximal housing 455 by an interference fit, an adhesive, a magnetic field, a weld, a threading, etc. In one or more embodiments, a first portion of fixation mechanism 230 may be fixed in fixation mechanism proximal housing 455 and a second portion of fixation mechanism 230 may be fixed in fixation mechanism distal housing 121, e.g., fixation mechanism proximal end 232 may be fixed in fixation mechanism proximal housing 455 and fixation mechanism distal end 231 may be fixed in fixation mechanism distal housing 121.

Illustratively, a portion of transitory element 100 may be disposed in a portion of actuation structure 410, e.g., a portion of outer base 105 may be disposed in instrument tip housing 430. In one or more embodiments, fixation mechanism 230 may be configured to fix a portion of transitory element 100 in a portion of actuation structure 410, e.g., fixation mechanism 230 may be configured to fix a portion of outer base 105 in instrument tip housing 430. Illustratively, fixation mechanism 230 may comprise a setscrew configured to screw into fixation mechanism distal housing 121 and fixation mechanism proximal housing 455. In one or more embodiments, fixation mechanism 230 may be permanently fixed in fixation mechanism distal housing 121, e.g., fixation mechanism distal end 231 may be fixed in distal housing 121 wherein removing fixation mechanism distal end 231 from distal housing 121 may be configured to damage a portion of transitory element 100. Illustratively, fixation mechanism distal end 231 may be permanently fixed in distal housing 121 wherein removing fixation mechanism distal end 231 from distal housing 121 may be configured to damage fixation mechanism distal receptacle 120. In one or more embodiments, fixation mechanism 230 may be temporarily fixed in fixation mechanism proximal housing 455, e.g., fixation mechanism proximal end 232 may be fixed in fixation mechanism proximal housing 455 wherein fixation mechanism proximal end 232 is removable from fixation mechanism proximal housing 455.

Illustratively, a first fixation mechanism proximal end 232 may be temporarily fixed in fixation mechanism proximal housing 455 wherein the first fixation mechanism proximal end 232 may be removed from fixation mechanism proximal housing 455 and a second fixation mechanism proximal end 232 may be inserted in fixation mechanism proximal housing 455. In one or more embodiments, a first fixation mechanism proximal end 232 may be temporarily fixed in fixation mechanism proximal housing 455 wherein the first fixation mechanism proximal end 232 may be removed from fixation mechanism proximal housing 455 and a second fixation mechanism proximal end 232 may be temporarily fixed in fixation mechanism proximal housing 455.

In one or more embodiments, a compression of actuation structure 410 may be configured to extend actuation structure distal end 411 relative to actuation structure proximal end 412. Illustratively, an extension of actuation structure distal end 411 relative to actuation structure proximal end 412 may be configured to extend nosecone 110 relative to handle base 105. In one or more embodiments, an extension of nosecone 110 relative to handle base 105 may be configured to extend hypodermic tube 240 relative to blank 250. Illustratively, an extension of hypodermic tube 240 relative to blank 250 may be configured to extend hypodermic tube distal end 241 over a portion of a first instrument jaw 260 and over a portion of a second instrument jaw 260. In one or more embodiments, an extension of hypodermic tube distal end 241 over a portion of a first instrument jaw 260 and over a portion of a second instrument jaw 260 may be configured to reduce a separation distance between the first instrument jaw 260 and the second instrument jaw 260. Illustratively, an extension of nosecone 110 relative to handle base 105 may be configured to expand pressure mechanism 130. In one or more embodiments, pressure mechanism 130 may be configured to provide a force that resists an extension of nosecone 110 relative to handle base 105, e.g., pressure mechanism 130 may be configured to provide a force that facilitates a retraction of nosecone 110 relative to handle base 105.

In one or more embodiments, a decompression of actuation structure 410 may be configured to retract actuation structure distal end 411 relative to actuation structure proximal end 412. Illustratively, a retraction of actuation structure distal end 411 relative to actuation structure proximal end 412 may be configured to retract nosecone 110 relative to handle base 105. In one or more embodiments, a retraction of nosecone 110 relative to handle base 105 may be configured to retract hypodermic tube 240 relative to blank 250. Illustratively, a retraction of hypodermic tube 240 relative to blank 250 may be configured to retract hypodermic tube distal end 241 off from a portion of a first instrument jaw 260 and off from a portion of a second instrument jaw 260. In one or more embodiments, a retraction of hypodermic tube distal end 241 off from a portion of a first instrument jaw 260 and off from a portion of a second instrument jaw 260 may be configured to increase a separation distance between the first instrument jaw 260 and the second instrument jaw 260. Illustratively, a retraction of nosecone 110 relative to handle base 105 may be configured to collapse pressure mechanism 130. In one or more embodiments, pressure mechanism 130 may be configured to provide a force that facilitates a retraction of nosecone 110 relative to handle base 105.

Illustratively, assembled instrument handle 600 may comprise a reusable instrument and assembled instrument tip 300 may comprise a single-use instrument. In one or more embodiments, a user may install a first assembled instrument tip 300 in assembled instrument handle 600 by inserting fixation mechanism proximal end 232 into fixation mechanism proximal housing 455, e.g., a user may install a first assembled instrument tip 300 in assembled instrument handle 600 by grasping tip cover 270 and rotating tip cover 270. Illustratively, a rotation of tip cover 270 may be configured to rotate fixation mechanism 230 within fixation mechanism proximal housing 455 until fixation mechanism 230 is temporarily fixed in fixation mechanism proximal housing 455. In one or more embodiments, a user may remove tip cover 270 from a portion of a first assembled instrument tip 300 by actuating tip cover 270 away from transitory element proximal end 102 after fixation mechanism 230 is temporarily fixed in fixation mechanism proximal housing 455. Illustratively, fixation mechanism proximal housing 455 may be configured to temporarily fix the first assembled instrument tip 300 in instrument tip housing 430, e.g., fixation mechanism proximal housing 455 may be configured to temporarily fix the first assembled instrument tip 300 in instrument tip housing 430 while the user performs a first surgical procedure. In one or more embodiments, the user may remove the first assembled instrument tip 300 from assembled instrument handle 600 by removing fixation mechanism proximal end 232 from fixation mechanism proximal housing 455, e.g., the user may remove the first assembled instrument tip 300 from assembled instrument handle 600 by grasping transitory element 100 and rotating transitory element 100. Illustratively, the user may install a second assembled instrument tip 300 in assembled instrument handle 600 by inserting fixation mechanism proximal end 232 into fixation mechanism proximal housing 455. In one or more embodiments, fixation mechanism proximal housing 455 may be configured to temporarily fix the first assembled instrument tip 300 in instrument tip housing 430, e.g., fixation mechanism proximal housing 455 may be configured to temporarily fix the first assembled instrument tip 300 in instrument tip housing 430 while the user performs a second surgical procedure.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   a handle having a handle distal end and a handle proximal end;
   an actuation structure of the handle having an actuation structure distal end and an actuation structure proximal end;
   a plurality of actuation arms of the actuation structure;
   a fixation mechanism proximal receptacle having a fixation mechanism proximal receptacle distal end, a fixation mechanism proximal receptacle proximal end, and a fixation mechanism proximal housing, the fixation mechanism proximal receptacle disposed in the actuation structure;
   an instrument tip housing of the actuation structure;
   an instrument tip having an instrument tip distal end and an instrument tip proximal end;
   a transitory element of the instrument tip having a transitory element distal end and a transitory element proximal end, wherein the transitory element is manufactured from a material configured to deform if the transitory element is sterilized in a medical autoclave;
   a fixation mechanism support of the transitory element;
   a fixation mechanism housing of the transitory element, the fixation mechanism housing disposed in the fixation mechanism support;
   a hypodermic tube of the instrument tip having a hypodermic tube distal end and a hypodermic tube proximal end wherein the hypodermic tube proximal end is disposed in the transitory element;
   a blank of the instrument tip having a blank distal end and a blank proximal end wherein the blank is disposed in the hypodermic tube and the fixation mechanism housing; and
   a fixation mechanism disposed in the transitory element and the fixation mechanism proximal housing wherein the fixation mechanism and the fixation mechanism proximal receptacle are configured to temporarily fix the instrument tip in the instrument tip housing.

2. The instrument of claim 1 further comprising:
   a nosecone of the transitory element having a nosecone distal end and a nosecone proximal end; and
   an outer base of the transitory element having an outer base distal end and an outer base proximal end wherein the outer base distal end is disposed between the nosecone distal end and the nosecone proximal end.

3. The instrument of claim 2 further comprising:
   a pressure mechanism of the transitory element having a pressure mechanism distal end and a pressure mechanism proximal end wherein the pressure mechanism is configured to provide a force.

4. The instrument of claim 1 further comprising:
   a tip cover having a tip cover distal end and a tip cover proximal end wherein the tip cover is configured to prevent damage to a portion of the blank.

5. The instrument of claim 1 wherein the blank is fixed in the fixation mechanism housing.

6. The instrument of claim 5 wherein a compression of the actuation structure is configured to extend the nosecone relative to the outer base.

7. The instrument of claim 6 wherein the compression of the actuation structure is configured to extend the hypodermic tube relative to the blank.

8. The instrument of claim 5 wherein a decompression of the actuation structure is configured to retract the nosecone relative to the outer base.

9. The instrument of claim 8 wherein the decompression of the actuation structure is configured to retract the hypodermic tube relative to the blank.

10. The instrument of claim 1 wherein the material has a melting point in a range of 158.0 to 212.0 degrees Fahrenheit.

11. The instrument of claim 1 wherein the material has a melting point of less than 140.0 degrees Fahrenheit.

12. The instrument of claim 1 wherein the transitory element is manufactured from a material configured to retain ethylene oxide.

13. The instrument of claim 12 wherein the material has a degree of crystallinity greater than 60.0 percent.

14. The instrument of claim 12 wherein the material is configured to retain less than 4.0 milligrams of ethylene oxide after a first sterilization by ethylene oxide and the mate-rial is configured to retain more than 4.0 milligrams of ethylene oxide after a second sterilization by ethylene oxide.

15. An instrument comprising:
   a handle having a handle distal end and a handle proximal end;
   an actuation structure of the handle having an actuation structure distal end and an actuation structure proximal end;
   a plurality of actuation arms of the actuation structure;
   a fixation mechanism proximal receptacle having a fixation mechanism proximal receptacle distal end, a fixation mechanism proximal receptacle proximal end, and a fixation mechanism proximal housing, the fixation mechanism proximal receptacle disposed in the actuation structure;

an instrument tip housing of the actuation structure;
an instrument tip having an instrument tip distal end and an instrument tip proximal end;
a transitory element of the instrument tip having a transitory element distal end and a transitory element proximal end wherein the transitory element is manufactured from a material configured to deform if the transitory element is sterilized in a medical autoclave;
a fixation mechanism support of the transitory element;
a fixation mechanism housing of the transitory element, the fixation mechanism housing disposed in the fixation mechanism support;
a hypodermic tube of the instrument tip having a hypodermic tube distal end and a hypodermic tube proximal end wherein the hypodermic tube proximal end is disposed in the transitory element;
a blank of the instrument tip having a blank distal end and a blank proximal end wherein the blank is disposed in the hypodermic tube and the fixation mechanism housing; and
a fixation mechanism disposed in the transitory element and the fixation mechanism proximal housing wherein the fixation mechanism and the fixation mechanism proximal receptacle are configured to temporarily fix the instrument tip in the instrument tip housing.

16. The instrument of claim 15 wherein the material has a melting point of less than 140.0 degrees Fahrenheit.

17. The instrument of claim 15 wherein the transitory element is manufactured from a material configured to retain ethylene oxide.

18. An instrument comprising:
a handle having a handle distal end and a handle proximal end;
an actuation structure of the handle having an actuation structure distal end and an actuation structure proximal end;
a plurality of actuation arms of the actuation structure;
a fixation mechanism proximal receptacle having a fixation mechanism proximal receptacle distal end, a fixation mechanism proximal receptacle proximal end, and a fixation mechanism proximal housing, the fixation mechanism proximal receptacle disposed in the actuation structure;
an instrument tip housing of the actuation structure;
an instrument tip having an instrument tip distal end and an instrument tip proximal end;
a transitory element of the instrument tip having a transitory element distal end and a transitory element proximal end wherein the transitory element is manufactured from a material configured to deform if the transitory element is sterilized in a medical autoclave and configured to retain ethylene oxide;
a fixation mechanism support of the transitory element;
a fixation mechanism housing of the transitory element, the fixation mechanism housing disposed in the fixation mechanism support;
a hypodermic tube of the instrument tip having a hypodermic tube distal end and a hypodermic tube proximal end wherein the hypodermic tube proximal end is disposed in the transitory element;
a blank of the instrument tip having a blank distal end and a blank proximal end wherein the blank is disposed in the hypodermic tube and the fixation mechanism housing; and
a fixation mechanism disposed in the transitory element and the fixation mechanism proximal housing wherein the fixation mechanism and the fixation mechanism proximal receptacle are configured to temporarily fix the instrument tip in the instrument tip housing.

19. The instrument of claim 18 wherein the material has a melting point of less than 140.0 degrees Fahrenheit.

* * * * *